United States Patent [19]

Starrett, Jr. et al.

[11] Patent Number: 5,212,294

[45] Date of Patent: May 18, 1993

[54] PRODUCTION OF 2′,3′-DIDEOXY-2′,3′-DIDEHYDRONUCLEOSIDES

[75] Inventors: John E. Starrett, Jr., Middletown; Muzammil M. Mansuri; John C. Martin, both of Cheshire, all of Conn.; Carl E. Fuller, Warners; Henry G. Howell, Jamesville, both of N.Y.

[73] Assignee: Bristol-Myers Squibb Company, New York, N.Y.

[21] Appl. No.: 860,938

[22] Filed: Mar. 31, 1992

Related U.S. Application Data

[60] Division of Ser. No. 697,512, Apr. 29, 1991, Pat. No. 5,130,421, which is a continuation of Ser. No. 441,023, Nov. 24, 1989, abandoned, which is a division of Ser. No. 173,473, Mar. 24, 1988, Pat. No. 4,904,770.

[51] Int. Cl.$^5$ .................... C07H 17/00; C07H 19/06
[52] U.S. Cl. ................................ 536/28.2; 536/28.3; 536/28.52; 536/28.5; 536/28.53; 536/28.54
[58] Field of Search .......................... 536/23, 24, 26

[56] References Cited

U.S. PATENT DOCUMENTS 3,322,747  5/1967  Shen et al. ................... 260/211.5

OTHER PUBLICATIONS

Ruyle et al., "Nucleosides, II. Reactions of 5′-Trityluridine 2′,3′-O-Thionocarbonate", *J. Organic Chemistry*, vol. 30(12), (1965), pp. 4353–4355.

Khwaja et al., "Fluorinated Pyrimidines. XXIX. syntheses of 2′,3′-Dehydro-5-fluoro-2′-deoxyuridine and 2′,3′-Dideoxy-5-fluorouridine[1]", *Journal of Medicinal Chemistry*, vol. 10 No. 6 (1967), pp. 1067–1069.

Barton et al., "Reactions of Relevance to the Chemistry of Aminoglycoside Antibiotics. Part 7. Conversion of Thiocarbonates into Deoxy-sugars", *Journal of The Chemical Society*, (1977), pp. 1718–1723.

Gibbs, "Facile high-yield synthesis of singly isomeric 2′3′-O-alkoxymethylidene adenosine", (1976), p. 4.

Adachi, "Synthetic Electrochemical Studies on Nucleosides. I. Novel Method for the Synthesis of 2′,3′,-Unsaturated Nucleosides via Electrolysis", *J. Org. Chem.*, vol. 44, No. 9 (1979), pp. 1404–1409.

Robins et al., "A Mild conversion of Vicinal Diols to Alkenes. Efficient Transformation of Ribonucleosides into 2′-ENE and 2′,3′-Dideoxynucleosides[1]", *Tetrahedron Letters*, vol. 25, No. 4, (1984) pp. 367–370.

*Primary Examiner*—John W. Rollins
*Attorney, Agent, or Firm*—Sandra M. Nolan

[57] ABSTRACT

There are disclosed novel processes for producing 2′,3′-dideoxy-2′3′-didehydronucleosides, for example, 2′,3′-dideoxy-2′,3′-didehydrothymidine in high yields and on a large scale. The compounds so-produced are useful as antiviral agents, especially as agents effective against the human immunodeficiency viruses (HIV).

6 Claims, No Drawings

PRODUCTION OF 2',3'-DIDEOXY-2',3'-DIDEHYDRONUCLEOSIDES

This application is a division of application Ser. No. 07/697,512, filed Apr. 29, 1991, U.S. Pat. No. 5,130,4; which was a continuation of application Ser. No. 07/441,023, filed Nov. 24, 1989, now abandoned; which was a division of application Ser. No. 07/173,473, filed Mar. 24, 1988, now U.S. Pat. No. 4,904,770.

BACKGROUND OF THE INVENTION

1. Field of the Invention

This invention relates to improved processes to produce 2',3'-dideoxy-2,'3'-didehydronucleosides.

2. Description of the Background and Related References

Acquired immunodeficiency syndrome (AIDS) is the result of an infection by human immunodeficiency virus(es) (HIV).[1] This retrovirus shows a specific tropism for the helper/inducer T cells[2] leading to their depletion. The resultant immunosuppression predisposes HIV patients to life-threatening opportunistic infections.

Although at present there is no cure for AIDS, one nucleoside derivative, 3'-azido-3'-deoxythymidine (AZT, Retrovir TM), has already proved to be an efficacious agent in the treatment of AIDS in clinical trials and has been licensed by the appropriate regulatory agency for use in patients with AIDS.[3] A number of other chemical and biological agents have been reported to have biological activity against HIV. 2',3'-Dideoxycytidine (ddC), 2',3'-dideoxyadenosine (ddA),[4] 2',3'-dideoxy-2',3'-didehydrocytidine (d4C),[5] suramine and its analogs,[6] ribavarin,[7] foscarnet,[8] HPA-23,[9] d-penicillamine,[10] castanospermine,[11] fusidic acid,[12] 3'-azidoguanosine (AZG),[13] and 3'-fluoro-3'-deoxythymidine (FDDT)[14] are all reported to be active against HIV.

A number of reports have appeared in the literature which have shown that 2',3'-dideoxy-2',3'-didehydrothymidine (d4T) possesses in vitro activity against HIV in several cell lines.[15]

2',3'-dideoxy-2',3'-didehydrothymidine (d4T) has been prepared by Horwitz et al. by two different routes.[16, 17] The first of these synthetic routes involves subjecting the 3',5'-anhydro derivative of thymidine to elimination reaction conditions. The second of these routes involves subjecting the 5'-O-protected 2,3'-anhydro nucleoside derivative of thymidine to ring-opening elimination reaction conditions.

The use of anhydro nucleosides as intermediates for nucleoside synthesis is well precedented in the literature in the art to which the present invention pertains.[18]

With the recent discovery of the potency of 2',3'-dideoxy-2',3'-didehydrothymidine (d4T) as an anti-HIV agent, a process which allows 2',3'-dideoxy-2',3'-didehydronucleosides, including d4T, to be prepared cheaply on a large scale becomes important.

The Horwitz route to produce d4T from the 3',5'-anhydro compound[16] is not feasible on a large scale because complete removal of the large volume of DMSO used in scale-up of the Horwitz procedure is very difficult to achieve and requires high vacuum (0.01 mmHg and heating for the temperature range of about 40°-50° C.) for an extended period of time. These conditions lead to cleavage of the glycosidic bond to give thymine as an undesired side product. Also, prolonged exposure to basic conditions, which are required when solvents other than DMSO (e.g. THF, DMF) are used leads to decomposition of d4T to, again, give thymine as an undesired side product.

The alternative Horwitz procedure requires protection of the 5'-OH position before formation of the 2,5'-anhydronucleoside. This 2,5'-anhydronuclesodie can be opened to give the 5'-O-protected nucleoside.

The desired 2,3'-anhydro nucleoside can be prepared directly by reacting thymidine with diethyl-(2-chloro-1,1-2-trifluoroethyl)amine.[19]

SUMMARY OF THE INVENTION

This invention is a process for producing 2',3'-dideoxy-2',3'-didehydronucleosides of the formula

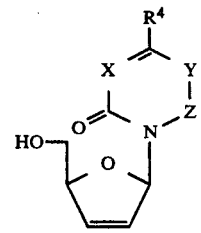

in high yields and on a relatively large scale.

DETAILED DESCRIPTION OF THE INVENTION

In one generic aspect, this invention is in a process for producing a 2',3'-dideoxy-2',3'-didehydronucleoside represented by the formula

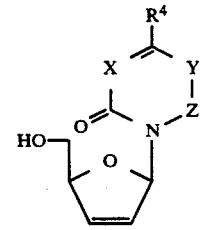

wherein the base moiety is a member selected from the group of unsubstituted and substituted bases consisting of pyrimidine, aza-pyrimidine, and deaza-pyrimidine; X is selected from N and C—H; Y is selected from C—$R^5$ and N; Z is selected from C—H and N; $R^4$ is selected from OH and $NH_2$; and $R^5$ is selected from H, unsubstituted and halo-substituted alkyl having the formula $C_nH_{2n}A$, and unsubstituted and halo-substituted alkenyl having the formula —$(CH_2)_m$—CH=CHA wherein m is an integer selected form 0, 1, 2 and 3, n is an integer selected from 1, 2, and 3 and A is selected from H, F, Cl, Br, and I, comprising the steps of:

(a) converting a 2'-deoxynucleoside represented by the formula

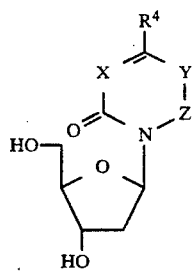

to a reactive 3',5'-anyhydro-2'-deoxynucleoside intermediate represented by the formula

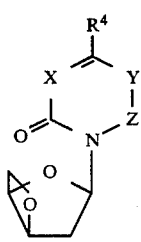

and (b) converting in the presence of strong base said reactive 3',5'-anhydro-2'-deoxynucleoside from step (a) above to said 2',3'-dideoxy-2',3'-didehydronucleoside; the improvement comprising:

(i) reacting said 3',5'-anhydro-2'-deoxynucleoside with a strong base selected from KOtBu, nBuLi, NaH, and LDA in the presence of a polar solvent selected from DMSO, THF, DMF, DME, and mixtures thereof;

(ii) triturating the resulting salt in the presence of an organic solvent;

(iii) collecting the solid crude salt intermediate from step (ii);

(iv) dissolving the salt from step (iii) in water;

(v) neutralizing the salt from step (iv); and (vi) obtaining the solid nucleoside free base product.

In another generic aspect, this invention is a process for producing a 2',3'-dideoxy-2',3'-didehydronuceloside represented by the formula

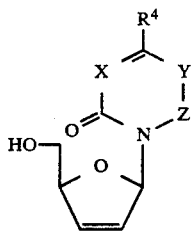

wherein the base moiety is a member selected from the group of unsubstituted and substituted bases consisting of pyrimidine, aza-pyrimidine, and deaza-pyrimidine; X is selected from N and C—H; Y is selected from C—$R^5$ and N; Z is selected from C—H and N; $R^4$ is selected from OH and $NH_2$; and $R^5$ is selected from H, unsubstituted and halo-substituted alkyl having the formula $C_nH_{2n}A$, and unsubstituted and halo-substituted alkenyl having the formula $C_nH_nA$, wherein n is an integer selected from 1, 2, and 3 and A is selected from H, F, Cl, Br, and I, comprising the steps of:

(a) converting a 2'-deoxynucleoside represented by the formula

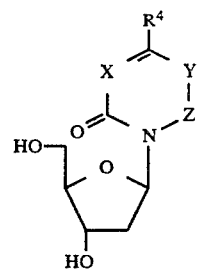

to a reactive 2,3'-anyhydro-2'-deoxynucleoside intermediate represented by the formula

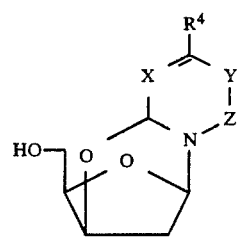

and (b) converting in the presence of base selected from non-nucleophilic and nucleophilic bases said reactive 2,3'-anhydro-2'-deoxynucleoside from step (a) above to said 2',3'-dideoxy-2'3'-didehydronuceloside.

In still another generic aspect, this invention is a process for producing 2',3'-dideoxy-2',3'-didehydronucleoside represented by the formula

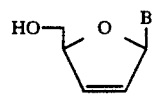

wherein B is a member selected from the group of bases consisting of purine, aza-purine, deaza-purine, pyrimidine, aza-pyrimidine, deaza-pyrimidine, and triazole ring bases, comprising the steps of:

(a) reacting a starting ribonucleoside represented by the formula

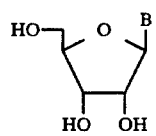

with trimethylorthoformate in the presence of a polar solvent under anhydrous conditions to obtain a reactive intermediate represented by the formula

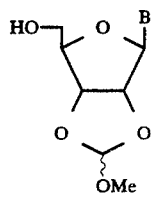

(b) subjecting the intermediate from step (a) to an elimination reaction by treatment with p-TsOH in Ac₂O at an elevated temperature of about 120°-160° C. for 4-8 hrs; and (c) deprotecting the resulting 5'-OAc group by treatment under mild base hydrolysis conditions.

In yet another generic aspect, this invention is a process for producing a 2',3'-dideoxy-2',3'-didehydronucleoside represented by the formula

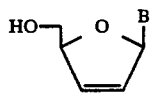

wherein B is a member selected from the group of bases consisting of purine, aza-purine, deaza-purine, pyrimidine, aza-pyrimidine, deaza-pyrimidine, and triazole ring bases, comprising the steps of (a) reacting a starting ribonucleoside represented by the formula

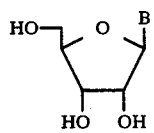

with a hydroxy protecting group reagent effective to selectively protect the 5'-hydroxyl (primary hydroxyl) group;

(b) reacting with 5'-OH-protected ribonucleoside from step (a) with a reagent selected from 1,1-thiocarbodiimidazole and thiophosgene under anhydrous conditions to obtain a reactive intermediate represented by the formula

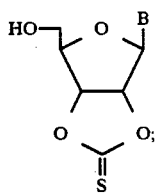

(c) subjecting the intermediate from step (6) to an elimination reaction by treatment with P(OEt)₃ in a polar solvent at an elevated temperature of about 140°-175° C. for about 0.5-4 hrs; and (d) deprotecting the resulting 5'-O-protecting group by treatment under mild acid hydrolysis conditions.

In yet another generic aspect, this invention is a process for producing a 2',3'-dideoxy-2',3'-didehydronuceloside represented by the formula

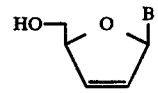

wherein B is a member selected from the group of bases consisting of purine, aza-purine, deaza-purine, pyrimidine, aza-pyrimidine, deaza-pyrimidine, and triazole ring bases, comprising the steps of:

(a) reacting a starting ribonucleoside represented by the formula

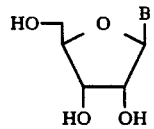

with an acyloxyisobutyryl bromide, preferably 2-acetoxyisobutyryl bromide, in a polar solvent under anhydrous conditions at an elevated temperature of about 75°-100° C. for about 1-3 hrs to obtain a reactive intermediate represented by formula

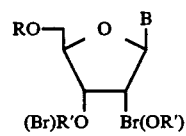

wherein R represents the acyloxyisobutyryl group and R' represents the acyl group of the acyloxyisobutyryl bromide;

(b) subjecting the intermediate from step (a) to an elimination reaction by treatment of said intermediate in an aprotic polar solvent with Zn/Cu reagent to obtain an intermediate represented by the formula

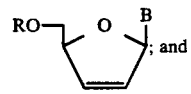

(c) deprotecting the 5'-O-protecting group in the intermediate from step (b) by treatment of said intermediate with a mild base, preferably methanolic ammonia, to give derived 2,3'-dideoxy-2',3'-didehydronucleoside.

As is described above, this invention concerns two embodiments of a process to produce 2',3'-dideoxy-2',3'-didehydronucleosides wherein the starting material is a 2'-deoxynucleoside and wherein the base component B is derived from a member selected from the group of bases consisting of is an unsubstituted or substituted pyrimidine, or aza-pyrimidine, or deaza-pyrimidine, preferably an unsubstituted or substituted pyrimidine. More preferably, the base moiety in these two embodiments is said unsubstituted or substituted pyrimidine corresponding to the formula and description set forth hereinbelow with respect to suitable unsubstituted and substituted pyrimidine bases. Still more preferably in these two embodiments, the base moiety is selected from thymine (5-methyl-2,6-dihydroxypyrimidine), cytosine (2-hydroxy-6-aminopyrimidine), uracil (2,6-dihydroxy-pyrimidine), and 5-ethyl- and 5-vinyl- and 5-halovinyl- and 5-halomethyl- and 5-haloethyl-2, 6-dihydroxypyrimidin-3-yl. Most preferably in these two embodiments the base moiety is thymine.

As is described above, this invention concerns three embodiments of a process to produce 2',3'-dideoxy-2',3'-didehydronucleosides wherein the starting material is a ribonucleoside and wherein the base component B is derived from a member selected from the group of bases consisting of unsubstituted and substituted purine, aza-purine, deaza-purine, pyrimidine, aza-pyrimidine, deaza-pyrimidine, and triazole ring bases. Preferably the base is selected from purine and pyrimidine bases. More preferably, the base is a pyrimidine base including one of the group of uracil and thymine.

Suitable unsubstituted and substituted purine bases include those purine bases represented by the structural formula

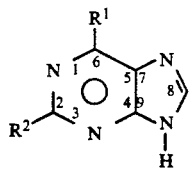

wherein $R^1$ and $R^2$ may be the same or different and are selected from hydrogen, hydroxy, halo (F, Cl, Br), amino, monoalkylamino, dialkylamino, alkoxy and cyano groups wherein the alkyl moiety is selected from $C_1$–$C_3$ alkyl groups.

Suitable unsubstituted and substituted pyrimidine bases include those pyrimidine bases represented by the structural formula

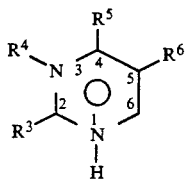

wherein R is selected from hydroxy, amino and sulfhydryl groups; $R^4$ is selected from hydroxy, amino and sulfhydryl groups $R^4$ is hydrogen; $R^5$ is selected from hydroxy and amino groups; and R6 is selected from hydrogen, $C_1$–$C_1$ alkyl, $C_2$–$C_3$ alkenyl, $C_2$–$C_3$ haloalkenyl having from 1 to 5 halo groups as defined herein, $C_2$–$C_3$ alkynyl, alkoxy wherein the alkyl moiety has 1–3 carbon atoms, cyano and halo (F, Cl, Br and I).

When derived from purine bases, representative of B are the following:
6-aminopurin-9-yl
2-aminopurin-9-yl
2,6-diaminopurin-9-yl
2-amino-6-hydroxypurin-9-yl (guanin-9-yl)
6-hydroxypurin-9-yl In addition to the above, the B component may be 2-halopurin-9-yl, 6-halopurin-9-yl, or 2,6-dihalopurin-9-yl, in which event the base component need not be activated, for example, completely silylated, in order to undergo the condensation or coupling reaction in step (e).

When derived from pyrimidine bases, representative of B are the following:
2,4-dihydroxyprimidin-1-yl
5-methyl-2,4-dihydroxypyrimidin-1-yl
5-ethyl-2,4-aminopyrimidin-1-yl
2-hydroxy-4-aminopyrimidin-1-yl
5-vinyl-2,4-dihydroxypyrimidin-1-yl
5-halovinyl-2,4-dihydroxypyrimidin-1-yl
5-haloethyl-2,4-dihydroxypyrimidin-1-yl
5-haloethyl-2,4-dihydroxypyrimidin-1-yl The above-mentioned 5-methyl and 5-ethyl substituents are representative of 5-alkyl substituents and the 5-vinyl substituent is representative of 5-alkenyl substituents. Examples of halo-groups on the 5-halovinyl (or 5-haloalkenyl) group include 1 to 4 F, Cl, and Br groups.

In the first-mentioned embodiment of the process according to this invention, the first step involves the preparation of a reactive 3',5'-anhydro-2'-deoxynucleoside, intermediate from a starting 2'-deoxynucleoside. This known intermediate is obtained by reacting a corresponding 2'-deoxynucleoside with sufficient, conventional activating hydroxyl protecting group reagent, e.g. MsCl or TsCl under conventional conditions to obtain a 3',5'-O-protecting group-2'-deoxynucleoside first intermediate and reacting said first intermediate with strong base selected from KOH and NaOH in a solvent selected from water and ethanol. Although any well known activating hydroxyl protecting group reagent useful in the art to which this invention pertains may be used, mesyl chloride is most advantageously used according to the procedure of Horwitz et al.

The second step of this embodiment involves an H-atom elimination reaction in the presence of strong base as is known and in the presence of polar solvent whereby the 3',5'-anydro ring is opened and the 2'-ene double bond is formed to obtain the desired 2',3'-dideoxy-2',3'-didehydronucleoside.

The invention in this first-mentioned embodiment of the process according to this invention is in the improvements in the selection, and handling and processing of the reactants and intermediates and products. Said improvement comprises:

(i) reacting said 3',5'-anhydro-2'-deoxynucleoside with a strong base selected from KOtBu, nBuLi, NaH, and LDA in the presence of a polar solvent selected from DMSO, THF, DMF, DME, and mixtures thereof and, preferably, at a temperature in the range of about 18°–80° C., more preferably about 18°–22° C.;

(ii) triturating the resulting salt in the presence of an organic solvent;

(iii) collecting the solid crude salt intermediate from step (ii);

(iv) dissolving the salt from step (iii) in water;

(v) neutralizing the salt from step (iv); and (vi) obtaining the solid nucleoside free base product.

In addition to the above-mentioned improvements in step (b), we have in step (a) found that by reducing the volume of solvent in the KOH addition and then by concentrating the slurry following neutralization to about 20% of its original volume, the desired intermediate precipitates and can be collected by filtration whereas the by-product KCL salt remains dissolved in the solvent. This obviates the need for hot acetone treatment of the completely evaporated step (a) reaction mixture to recover the reactive intermediate.

An alternative approach to making the desired 2',3'-dideoxy-2',3'-didehydronucleosides from the corresponding 2'-deoxynucleoside would be to start from the corresponding ribonucleoside. Accordingly, we have discovered that we can treat uridine, with trimethyl orthoformate to obtain the corresponding ortho ester reactive intermediate.

In step (ii) of the above first-mentioned embodiment, the solvent used may be any organic solvent compatible with the reactants and intermediate salt resulting from step (i). Preferably, the solvent is selected from toluene, acetone, and ethyl acetate, most preferably toluene. The temperature of the trituration procedure in step (ii) preferably is about 0°–10° C., most preferably about 0°–4° C.

In the second-mentioned embodiment of the process according to this invention, the first step involves the preparation of the known reactive 2,3'-anhydro-2'-deoxynucleoside intermediate by reacting a starting corresponding 2-deoxynucleoside with a strong base effective to form a 2,3'-anhydro-2'-deoxynucleoside. A suitable reagent to accomplish this ring formation is the known reagent, diethyl(2-chloro-1,1,2-trifluoroethyl)amine. This known intermediate has been reacted with nucleophiles to obtain substituted, nucleosides such as, for example, 3'-azido-2', 3'-dideoxythymidine (AZT).[20]

The second step of this embodiment involves not nucleophilic addition but, rather, the ring opening reaction of the anhydro ring of the above reactive intermediate. Suitable reagents to effect this ring opening are either non-nucleophilic bases such as tetrabutyl ammonium fluoride or nucleophilic bases selected from KOtBu, NaOH, KOH and the like.

In the third-mentioned embodiment of the process according to this invention, the first step involves reacting a starting ribonucleoside with trimethylorthoformate in the presence of a polar solvent under anhydrous conditions[21,22] to obtain an ortho ester reactive intermediate represented by the formula

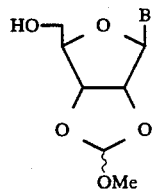

The next step involves subjecting the reactive intermediate to an elimination[23] reaction by treatment with an organic acid, e.g. p-TsOH, in Ac₂O at an elevated temperature of about 120°–160° C. for about 4–8 hours. Finally, the last step involved deprotecting the resulting 5'-OAc group of the ortho ester reactive intermediate by treatment under mild base hydrolysis conditions.[15b]

In the fourth-mentioned embodiment of the process according to this invention, the first step involves reacting a starting ribonucleoside with one of any conventional hydroxy protecting groups effective to selectively protect the 5'-hydroxyl group (i.e., the primary hydroxyl group as distinguished from the sugar-ring-bound secondary hydroxy groups). The second step involves reacting the 5'-O protected ribonucleoside with one of 1,1-thiocarbonyldiimdazole and thiophosgene under anhydrous conditions to obtain a reactive thiocarbonate intermediate represented by the formula

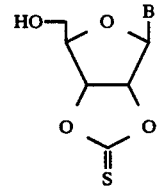

The next step involves subjecting the reactive intermediate to an elimination reaction by treatment with P(OEt)₃ in a polar solvent at an elevated temperature of about 140°–175° C. for about 0.5–4 hrs. Finally, the fourth and last step involves deprotecting the resulting 5'-O-protecting group of the reactive thiocarbonate intermediate by treatment under mild acid hydrolysis conditions.

In the fifth and last-mentioned embodiment of the process according to this invention, the first step involves reacting a starting ribonucleoside with 2-acetoxyisobutyryl bromide[24] to obtain the reactive intermediate represented by the formula

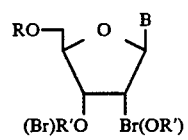

Next, the reactive intermediate mixture is reacted with Zn/Cu reagent in an aprotic polar solvent to effect elimination to obtain the desired 2',3'-dideoxy-2',3'-didehydronucleoside product.[25]

SCHEME I illustrates schematically typical, representative processes according to our present invention. Route A illustrates the first-mentioned embodiment proceeding through the 3',5'-anhydro, or "oxetane", reactive intermediate. Route B illustrates the second-mentioned embodiment proceeding through the 2,3'-anydro reactive intermediate. Both of Routes A and B start from a 2'-deoxynucleoside Route C illustrates the third- and foruth-mentioned embodiments proceeding from a starting ribonucleoside through an ortho ester or thiocarbonate reactive intermediate, respectively. Route D illustrates the last-mentioned embodiment proceeding through a 3'-O-acetyl-2'-bromo-2'-deoxynucleoside and/or 3'-bromo-2'-O-acetoxy intermediate.

SCHEME I

ROUTE A:

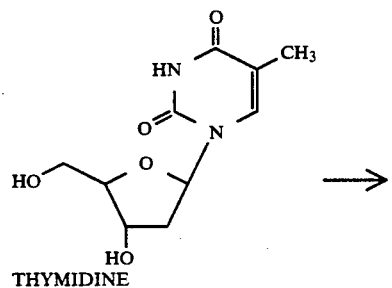

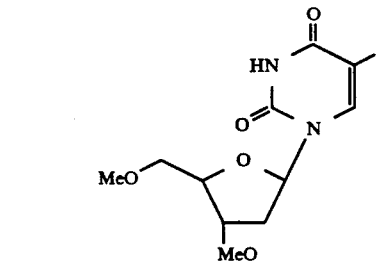

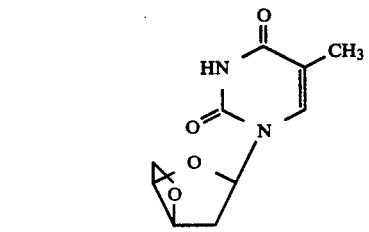

-continued
SCHEME I

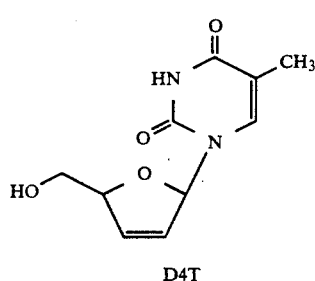

D4T

ROUTE B:

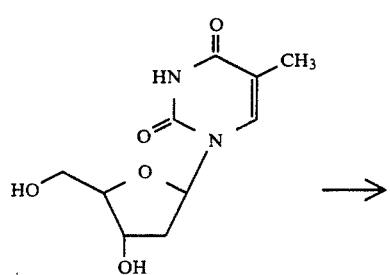

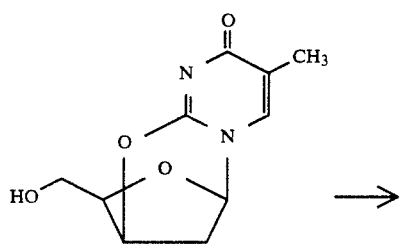

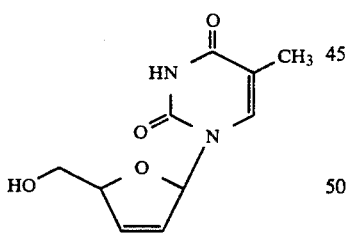

ROUTE C:

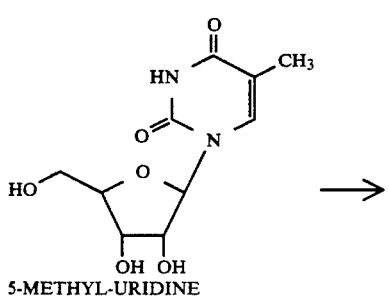

5-METHYL-URIDINE

-continued
SCHEME I

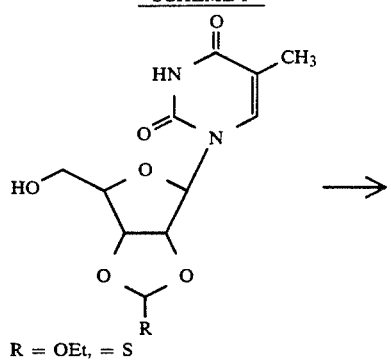

R = OEt, = S

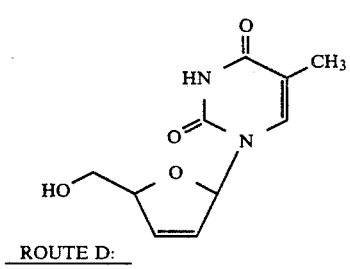

ROUTE D:

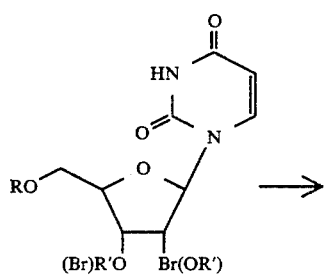

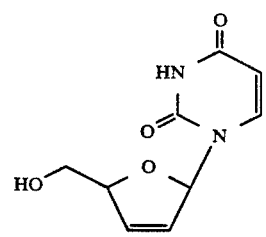

The problems presented when attempting to practice the so-called "oxetane" route according to Horwitz et al. which proceeds through the 3',5'-anhydro intermediate are associated mainly with scale-up of the final elimination reaction. On larger scales removal of the solvent leads to thymine elimination on account of prolonged exposure to heat. The use of larger amounts of base also gives thymine as an undesired product.

The specific improvements made to this "oxetane" route which constitute one embodiment of our invention involve (1) utilizing a much smaller amount of water in converting the mesylate to the oxetane, thereby carrying-out the reaction under more concentrated conditions, and (2) modifying the work-up of the final step wherein we precipitate by means of trituration the potassium salt from the final step involving KOtBu/DMSO treatment of the reactive intermediate. In addition, the workup of step (a) has been simplified to neutralizing the reaction, reducing the amount of water and collecting the resulting product. This is much easier than completely removing the water, suspending the resulting salts in hot acetone, filtering, then stripping the filtrate. This allows the product to be collected, neutralized and re-collected. The advantage of our improvements over the literature procedures is that removal of large volumes DMSO under vacuum is not required and, also, that lengthy heating which destroys the product but which otherwise is required to remove DMSO under vacuum is avoided. As a result of these improvements, relatively pure product is obtained on bulk scale.

The problems in the literature methods for producing the desired 2',3'-dideoxy-2',3'-didehydronucleosides by way of the 2,3'-anhydro reactive intermediate involve the use of diethyl(2-chloro-1,1,2-trifluoroethyl)amine, a fluoramine reagent that is difficult to make and which requires specialized equipment. Alternatively, the literature reports a lengthy 4-step procedure involving 5'-O-tritylation, 3'-O-mesylation, detritylation, and anhydro formation. The literature reports formation of various products and side-products other than the desired 2',3'-dideoxy-2',3'-didehydronucleoside products The specific improvements made in the published route proceding through the 2,3'-anhydro reactive intermediate involve the discovery that the use of the reagent, tetrabutyl ammonium fluoride (TBAF), under non-nucleophilic conditions affords the desired product cleanly and in high yields. Alternatively, the use of KOtBu/DMSO and NaOH/DMF, but not NaCN/DMF or DBU/DMF or NaOH/MeOH or KOtBu/BuOH, in place of TBAF in THF or DMF affords the desired product although yields are lower and some undesired side-product (3'-epi-thymidine) was obtained with the use of NaOH/DMF.

Thus, the processes according to this invention are useful for the preparation of a variety of 2'3'-dideoxy-2',3'-didehydronucleosides, especially pyrimidine and purine nucleosides, having antiviral, antimetabolic, and antineoplastic activity as well as activity against human immunodeficiency viruses.

The following examples illustrate but a few representative embodiments of the processes according to this invention and are set forth to teach those skilled in the pertinent art how to practice this invention and are not to be construed as limiting in scope. All parts and percentages are by weight and temperatures are in degrees Celsius unless otherwise specified.

Biological data, including anti-HIV data, of d4T produced by a process according to this invention are set forth in TABLE I. These data are consistent with data published.

REFERENCES 1. (a) Barre-Sinoussi, F; Chermann, J. C.; Rey, R.; Nugeyre, M. T.; Chamaret, S.; Gruest, C.; Dauguet, C.; Axler-Blin, C.; Rouzioux, C.; Rozenbaum, W.; Montagnier, L. *Science* (Washington, D.C.) 1983, 220, 868–871. (b) Broder, S.; Gallo, R. C. *N. Engl. J. Med.* 1984, 311, 1292-1297. (c) Broder, S; Gallo, R. C. *Annu. Rev. Immunol.* 1985, 3, 321–336.
2. Popovic, M.; Sarngadharan, M. G.; Read E.; Gallo, R. C. *Science* (Washington D. C.) 1984, 224, 497–500. (b) Gallo, R. C.; Sarngadharan, M. G.; Popovic, M.; Shaw, G. M.; Hahn, B.; Wong-Stahl, F.; Robert-Guroff, M.; Salahaddian, Z., Markham, P. D. *Prog. Allergy* 1986, 37, 1–45.
3. Fischl, M. A.; Richman, D. D.; Grieco, M. H.; Gottlieb, M. S.; Volberding, P. A.; Laskin, O. L.; Leedom, J. M.; Groopman, J. E.; Mildvan, D.; Schooley, R. T.; Jackson, G. G.; Durack, D. T.; King, D. *New Engl. J. Med.*, 1987, 317, 185.
4. Mitsuya, H.; Broder, S. *Proc. Natl. Acad. Sci. U.S.A.* 1986, 83. 1911–1915.
5. (a) Lin, T. S.; Shinazi, R.; Chen, M. S.; Kinney-Thomas, E.; Prusoff, W. H. *Biochem. Pharmacol.* 1987, 36, 311. (b) Balzarini, J.; Pauwels, R.; Herdewijn, P.; De Clercq, E.; Cooney, D. A.; Kang, G-J.; Dalal, M.; Johns, D. G.; Broder, S. *Biochem. Biophys. Res. Comm.* 1986, 140. 735.
6. Cheson, B. D.; Levine, A. D.; Mildvan, D.; Kaplan, L. D.; Wolfe, P.; Rios, A.; Groopman, J.; Gill, P.; Volbdering, P. A.; Poiesz, B. J.; Gottlieb, M. S.; Holden, H.; Volsky, D. J.; Silver, S. S.; Hawkins, M. *J. J. Amer. Med. Assoc.* 1987, 258, 1347.
7. (a) Balzarini J.; Mitsuya, H.; De Clercq, E.; Broder, S. *Int. J. Med,* 1980, 37 451. Mitchell, S. W.; Hicks, D. R. *Lancet* 1984, ii. 1367.
8. (a) Sarin, P. S.; Taguchi, Y.; Sun, D.; Thornton, A.; Gallo, R. C.; Oberg, B. *Biochem. Pharmacol.* 1985, 34, 4075. (b) Sandstrom, E. G.; Kaplan, J. C.; Byington, R. E.; Hirsch, M. s. *Lancet* 1985, i, 480.
9. Lane, H. C.; Fauci, A. S. *Ann. Intern. Med.* 1985, 103, 714.
10. Chandra, P.; Sarin, P. S. *Arznrim-Forsch/Drug Res.* 1986, 36, 184.
11. Tyms, A. s.; Berrie, E. M.; Ryder, T. A.; Nash, R. J.; Hegarty, M. P.; Taylor, D. L.; Mobberley, M. A.; Davis, J. M.; Bell, E. A.; Jeffries, D. A.; Taylor-Robinson, D.; Fellows, L. E. *Lancet* 1987, ii, 1025.
12. Faber, V.; Newell, A.; Dalgleish, A. G.; Malkovsky, M. *Lancet* 1987, ii. 827.
13. (a) Hartmann, H.; Hunsmann, G.; Eckstein, F. *Lancet* 1987, i, 40. (b) Baba, M.; Pauwels, R.; Balzarini, J.; Herdewiijn, P.; De Clercq, E. *Biochem. Biophys. Res. Comm.* 1987, 145, 1080.
14. (a) Herdewijn, P.; Balzarini, J.; De Clercq, E.; Puwels, R.; Baba, M.; Broder, S.; Vanderhaeghe, H. *J. Med. Chem.* 1987, 30, 1270. (b) Mattes, E.; Lehmann, C.; Scholz, D.; von Janta-Lipinski M.; Gaertner, K.; Rosenthal, H. A.; Langen, P. *Biochem. Biophys. Res. Comm.* 1987, 148, 78. (c) Polski, B.; Gold, J. M. W.; Hardy, W. D.; Baron, P. A.; Zuckermann, E. e.; Chou, T-C.; Levine, S. M.; Flomenberg, N.; Wang, L.; Watanabe, K. A.; Fox, J. J.; Armstrong, D. *27th ICAAC* 1987, Abstract 368, p161.
15. (a) Lin, T. S.; Chen, M. S.; Gao, Y-S.; Ghazzouli, I.; Prusoff, W. H. *J. Med. Chem.* 1987, 30, 440. (b) Lin, t. S.; Shinazi, R. F.; Prusoff, W. H. *Biochem. Pharmacol.* 1987, 17, 2713. (c) baba, M.; Pauwels, R.; De Clercq, E.; Desmyter, J.; Vandeputte, M. *Biochem. Biophys. Res. Comm.* 1987, 142, 128. (d) Balzarini, J.; Kang, G-J.; Dalal, M.; Herdewjin, P.; De Clercq, E.; Broder, S.; Johns, D. G. *Mol. Pharmacol.* 1987, 32, 162. (e) Hamamoto, Y.; Nakashima, H.; Matsui, T.; Matsuda, A.; Ueda, t.; Yamamoto, N. *Amtimicrob. Agents Chemother.* 1987, 31, 907.

16. Horwitz, J.; Chua, J. in "Synthetic Procedures in Nucleic Acid Chemistry" (Vol. 1), Zorbach, W. W.; Tipson R. S. (eds); Interscience, New York, p. 344.
17. Horwitz, J.; Chua, J.; Da Rooge, M. A.; Noel, M.; Klundt, I. L. *J. Org. Chem.* 1966, 31, 205.
18. Fox, J. J.; Miller, N. C. i J. Org. Chem., 1963, 28, 936.
19. Kowollik, G.; Gaertner, K.; Langen, P. *Tetrahedron Lett.*, 1969, No. 44, 3863.
20. Glinski, R. P.; Khan, M. S.; Kalamas, R. L.; Sporn, M. B. *J. Org. Chem.*, 1973, 38, 4299.
21. Davisson, V. J.; Davis, D. R., Dixit, V. M.; Poulter, C. D., *J. Org. Chem.*, 1987, 52, 1794.
22. Griffin, B. E.; Jarman, J.; Reese, C. B.; Sulston, J. *Tetrahedron*, 1967, 23, 230.
23. Ando, M.; Ohhara, H.; Takase, K. *Chem. Lett.*, 1986, 879.
24. Jain, T. C.; Jenkins, I. D.; Russell, A. F.; Verheyden, J. P. H.; Moffatt, J. H., *J. Org. Chem.*, 1974, 39, 80.

EXPERIMENTAL

Melting points were determined on an Electrothermal capillary apparatus and are uncorrected. TLC was performed on silica gel 60 F-254 plates purchased from E. Merck and Co., and column chromatography was performed on flash silica gel (40 uM particle size, Baker), Elemental analysis were performed by the analytical department, Bristol Myers, Wallingford. $^1$H and $^{13}$C NMR spectra were recorded AM360 Bruker NMR spectrometer using tetramethylsilane as the internal standard; chemical shifts are recorded in parts per million. Analytical HPLC was performed on a Waters C18 reverse phase coloumn.

3′,5′-Di-O-(methanesulfonyl)thymidine

A 3 liter, 3 necked round-bottomed flask was equipped with an overhead stirrer and paddle, a 500 mL dropping funnel and a Claisen adapter containing a drying tube and a thermometer. Thymidine (200 g, 0.82M) and pyridine (750 mL) were added to the flask. The mixture was stirred and warmed with a water bath (20 mins) to give a clear solution. The solution was then cooled in an ice bath to 0°–3° C. and the dropping funnel was charged with methanesulfonyl chloride (206.5 g, 1.08M). The methanesulfonyl chloride was then added dropwise over 40 minutes with no noticeable exotherm. The solution was stirred at 0° C. for 1 hr and then stored at 5° C. for 18 hr. The light brown mixture was then poured onto rapidly stirred water (3 L) containing ice (approx. 500 g). The desired product crystallised immediately. After stirring for 0.5 hr, the product was collected by filtration and washed several times with water (3×100mL). The white solid was then dried under vacuum overnight (crude weight, 322 g, 98% yield). The product was recrystallised from hot acetone to give 267 g of a white solid (81% yield), mp 169°–171° C. (lit. 170°–171° C.) $^1$H NMR (360 MHz, d$_6$-DMSO) 11.40 (s, 1H, NH), 7.50 (s, 1H, H-6), 6.21 (t, 1H, H-1′), 5.29 (m, 1H, H-3′), 4.45 (m, 2H, H-5′), 4.35 (m, 1H, H-4′), 3.31 (s, 6H, SO$_2$CH$_3$), 2.50 (m, 2H, H-2′), 1.78 (s, 3H, CH$_3$). Analysis (C$_{12}$H$_{18}$N$_2$O$_9$S$_2$) C, H, N.

1-(3,5-Anhydro-2-deoxy-β-D-threo-pentofuranosyl)thymine

3′,5′-Di-O-(methanesulfonyl)thymidine (248 g, 0.62M) was added in portions to a stirred solution of sodium hydroxide (74.7 g, 1.87M) in water (1.6 L). On addition 3 the reaction mixture became a yellow-orange solution. This stirred solution was then heated to reflux for 2 hr. Once the reaction mixture had cooled to room temperature, 6N hydrochloric acid (100 mL) was added. The reaction mixture was concentrated in vacuo by removing 1.3 L of water. The resulting slurry was cooled in an ice bath for 2 hr. The solid was then filtered and washed sparingly with ice water, and then vacuum dried to constant weight (103.7 g, 74%). The product 3, mp 188°–190° C. (lit. 190°–193° C.) was used without further purification. $^1$H NMR (360 MHz, d$_6$-DMSO) 11.35 (s, 1H, NH), 8.01 (s, 1H, H-6), 6.49 (q, 1H, H-1′), 5.47 (m, 1H, H-3′), 4.88 and 4.67 (m, 2H, H-5′), 4.22 (d, 1H, H-4′), 2.47 (m, 2H, H-2′) 1.77 (S, 3H, CH$_3$). $^{13}$C NMR (75 MHz, d$_6$-DMSO) 163.64 (C2), 151.10 (C4), 136.57 (C6), 109.62 (C5), 88.29 (C4′), 86.85 (C1′), 79.83 (C3′), 75.14 (C5′), 37.17 (C2′), 12.33 (CH$_3$). Analysis (C$_{10}$H$_{12}$N$_2$O$_4$) C, H, N.

1-(2,3-Dideoxy-β-D-glycero-pent-2-enofuranosyl)thymine

To a 3-necked, 1 L round-bottomed flask equipped with a mechanical stirrer, thermometer and nitrogen inlet was added dry DMSO (400 mL) and oxetane (90.0 g, 0.402M). To this solution was added 97% KOtBu (74 g, 0.643M) in 1.5 g portions over 25 minutes. The temperature was maintained between 18° C. and 22° C. by means of an external ice bath. After the addition was complete the reaction was stirred for a further 1 hr and no further rise in temperature was observed and TLC indicated that the reaction was approximately 90% complete. The reaction was stirred at 21° C. for 16 hr, after which time TLC indicated that the reaction was complete. The viscous solution was poured onto cold (4° C.) toluene (3 L), resulting in a beige colored precipitate. The temperature of the mixture rose to 7° C. upon addition of the DMSO solution. The mixture was occasionally swirled over 20 minutes, then filtered on a 18.5 cm Buchner funnel. The collected yellowish solid was washed twice with cold toluene and allowed to dry under suction for 1 hr. The solid was dissolved in 300 mL of water, whereupon two layers formed. The mixture was placed in a separatory funnel and the upper layer (containing residual toluene) was discarded. The aqueous layer was placed in a 1 L beaker equipped with a pH probe, magnetic stirring bar and thermometer. The temperature was cooled to 10° C. by the use of an external ice bath. Concentrated HCl was added dropwise to the stirred solution at a rate in which the temperature was kept below 15° C. After the addition of HCl (50.5 mL, 0.61M) the pH=7±0.1 and a precipitate began to form. To this thick mixture was added potassium chloride (70 g) and stirring was continued at 5° C. for 1 hr. The precipitate was collected and sucked dry for 2 hr, then air dried for 16 hr. The solid was crushed up and slurried in hot acetone (500 mL) and filtered. The residue in the filter paper was rinsed with hot acetone (2×200 mL), then slurried again with hot acetone (300 mL), filtered, and washed once more with hot acetone (2×100 mL). The combined filtrate was concentrated to dryness to give 51.3 g (57%) of d4T as an off-white solid, mp 165°–166° C. [α]$_D^{20}$-46.1 (c0.7, water). $^1$H NMR (360 MHz, d$_6$-DMSO) 11.29 (s, 1H, NH), 7.63 (s, 1H, H-6), 6.80 (d, 1H, J=1.2 Hz, H-1′), 6.38 (d, 1H, J=5.9 Hz, H-3′), 5.90 (dd, 1H, J=1.1, 4.7 Hz, H-3′), 5.01 (m, 1H, OH), 4.76 (s, 1H, H-4′), 3.60 (dd, 2H, J=4.8, 3.6 Hz, H-5′), 1.71 (d, 3H J=1.2 Hz, CH$_3$). $^{13}$C NMR (75 MHz, d$_6$-DMSO) 164.42 (C4), 151.30 (C2), 137.23 (C2′), 135.36 (C3′), 126.35 (C6), 109.33 (C5), 89.15 (C1'), 87.56 (C4'), 62.41 (C5'), 12.15 (C5CH3). MS m/e (methane DCI) (relative intensity) 225 (M+H, 20), 207 (15), 193 (8), 155 (13), 127 (100), 99 (20). IR (cm$^{-1}$) 3463, 3159, 3033, 1691, 1469, 1116, 1093. Anal. (C$_{10}$H$_{12}$N$_2$O$_4$) C,H,N.

1-(2,3-Dideoxy-β-D-glcero-pent-2-enofuranosyl)thymine

Tetrabutyl ammonium fluoride (0.22 mL, 0.22 mM, 1.0M) added to a suspension of the anhydronucleoside 25 mg, 0.11 mM) in dry THF (3 mL). After stirring at 22° C for 3 hr, the TLC showed only starting material. The mixture was heated to reflux for 18 hr, at which time the reaction appeared to be complete. After cooling, the solvents were removed in vacuo and the residue was dissolved in CH$_2$Cl$_2$/MeOH/NH$_4$OH (90:10:1). Purification was performed on a 20 mm flash chromatography column, eluting with CH$_2$Cl$_2$MeOH/NH$_4$OH (90:10:1). Concentration of the fractions containing the product afforded 18 mg (72%) of d4T.

1-(5'-O-trityl-2',3'-thiocarbonylribofuranosyl)uracil

5'-O-Trityluridine (10.6 gm., 22 mM) was added to a dry 250 mL round-bottomed flask under an argon atomosphere. Dry tetrahydrofuran (110 mL) was added and the reaction mixture stirred until it became homogeneous. When 1,1-thiocarbonyldiimidazole (4.3 gm., 27 mM) was added to the solution the reaction became yellow and was then allowed to stir at room temperature for 72 hrs. The solvent was removed in vacuo and the resulting syrup flash chromatographed on silica with ethyl acetate/hexane (75:25) as eluent. The produce was isolated and then recrystallized from absolute ethanol to give an off white powder (0.8. gm., 77%). $^1$H NMR (360 Mhz, CDCl$_3$) 8.9 (br s, 1H, NH), 7.3 (m,16H, 3×C$_6$H$_5$H6), 5.7 (d, 1H, H5), 5.6 (m, 2H, H2', H3'), 5.4 (m, 1H, H1'), 3.4 (q, 2H, H5').

5'O-Trityl-2',3'-dideoxy-2',3'-didehydrouridine 1-(5'-O-Triyl-2',3'-thiocarbonylribofuranosyl)uracil (6.0 gm., 11.5 mM.) was added to triethyl phosphite (30 mL). The triethyl phosphite had been preheated to 160° C. The reaction mixture was heated at 160° C. for 1 hr. The solvent was then removed in vacuo and then the resultant glassy solid was flash chromatographed on silica with ethyl acetate/hexane (75:25) as eluent. The desired product was isolated from the column and then recrystallized from ethyl acetate/hexane and then collected as a white solid (2.0 gm.40%). M.p. 188°-191° C. $^1$H NMR (360 Mhz, CDCl$_3$) 8.95 (br2, 1H, NH), 8.00 (d, 1H, H6), 7.5 (m, 15H, 3×C$_6$H$_5$), 7.2 (m, 1H, H1') 6.7 (m, 1H, H2'), 6.05 (m,1H, H3'), 5.2 (dd, 1H, H5), 5.10 (br s, 1H, H4'), 3.6 (m, 2H, H5').

2',3'-Dideoxy-2',3'-didehydrouridine (d4U)

5'O-trityl-2',3'-dideoxy-2',3'-didehydrouridine (0.5 gm.,1.1 mM) was dissolved in a chloroform (10 mL) and methanol (2 mL) mixture containing 2% p-toluenesulphonic acid. The reaction mixture was stirred at room temperature for 0.75 hr., and then neutralized with 2N NaOH (0.5 mL). The solvent was removed in vacuo and the residue chromatographed on silica using chloroform/acetone (2:1) as eluent. The desired product was isolated as a white crystalline solid with the same physical and spectroscopic characteristics as d4U produced by an alternative method. M.p. 155° C. $^1$H NMR (360 Mhz, D$_2$O/DMSO) 7.8 (d, 1H, H6), 6.7 (m, 1H, H1'), 6.37 (m, 1H, H2'), 5.8 (m, 1H, H3'), 5.56 (d, 1H, H5), 4.7 (m, 1H, H4'), 3.6 (m, 2H, H5'). $^{13}$C NMR (70 Mhz, D$_2$O/DMSO) 163 (C4), 151 (C2), 141 (C2'), 135 (C3'), 126 (C6), 101 (C5), 89 (C1'), 87 (C4'), 62 (C5').

2',3'-Methoxymethylideneuridine

Uridine (50 gm.,.205M) was added to a 1 liter round-bottomed flask under an nitrogen atmosphere. Dry freshly distilled tetrahydrofuran (500 mL), pyridinium p-toluene sulphonate (5 gm., 20 mM) were added to the reaction mixture. Trimethyl orthoformate (109 gm.,1.03M) was then added slowly via an addition funnel. The reaction mixture was left to stir for 18 hr. at ambient temperature during which time the reaction became homogeneous. Water (18 gm., 1M) was added and the reaction stirred for a further 0.5 hr. after which time pyridine (20 mL) was added. The reaction was stirred at ambient temperature for another 18 hr. and the solvents then removed in vacuo. The resultant white solid was flash chromatographed on silica to give the desired product as a white solid (40 gm.68%). M.p. 188°-190° C. (lit. 189°-190° C.).

5-O-Acetyl-2',3'-dideoxy-2',3'-didehydrouridine

The methoxymethylidene compound (11.8 gm.,41 mM) was dissolved in acetic anhydride (110 mL) and p-toluene sulphonate (20 mgs) added and the reaction heated to 140° C. for 6 hr. The reaction was allowed to cool and triethylamine (1 mL) added. The solvents were removed in vacuo and the product was chromatographed on silica using chloroform/acetone (4:1) as eluent to give the desired product as a clear oil. $^1$H NMR (360 Mhz DMSO) 11.3 (br s, 1H, NH), 7.4 (d, 1H, H6), 6.8 (m, 1H, H1'), 6.4 (m, 1H, H2'), 5.9 (m, 1H, H3'), 5.6 (d, 1H, H5), 5.0 (m, 1H, H4') 4.2 (m, 2H, H5'), 2.0 (s, 3H, CH$_3$).

5'-O-(2'-Acetoxyisobutryl)3-O-acetyl-2'-bromo-2'-deoxyuridine

Uridine (5.0 g, 0.021M.) was suspended in acetonitrile (90 mL) and 2-acetoxyisobutyrl bromide (12.85 g, 0.063M) added over 15 minutes and the reaction heated at 80° C. for 3 hrs. The homogeneous solution was cooled to room temperature and the solvent removed in-vacuo. The resulting syrup was dissolved in EtOAc (200 mL) and washed with NaHCO$_3$ (3×100 mL). The organic layer was dried over MgSO$_4$ and the solvent removed in-vacuo. Chromatography on SiO$_2$ (75%EtOAc/25%Hex) gave 6.7 g of a white foam. (67%) m.p. 68°-70° C.

2',3'-dihydro-2',3'-dideoxyuridine (D4U)

The bromouridine (2 g, 4.2 mM) was dissolved in 3 ml.DMF and was added dropwise to a slurry of Zn/Cu (0.70 g, 10.5 mM.) in dry DMF (25 mL). The reaction was stirred for 2.5 hrs. at room temperature when no starting material was observed by TLC. The reaction was filtered through celite and the filtrate concentrated in-vacuo in a high-vacuum system at 20° C. The resulting white solid (1.1 g, 85%) was dissolved in MeOH and cooled to 0° C. with an ice-water bath. Anhydrous ammonia was bubbled in for 20 minutes and the solution warmed to 60° C. over 18 hrs. TLC revealed a spot corresponding to D4U. The solvents were removed and the resulting white solid chromatographed on SiO2(10-%MeOH/CH2CL2) to yield gr. (55%) of the desired product. m.p. 155° C.

TABLE 1

Comparative in vitro anti-HIV efficacy[a] and cellular toxicity[b] of AZT and d4T.

| Compound | ID$_{50}$[c] (μM) | TCID$_{50}$[d] (μM) |
|---|---|---|
| AZT | 0.45 | 54.0 |
| d4T | 0.33 | 39.0 |
| (Example p. 28) | | |

[a]The antiviral test was performed on HIV (LAV strain)-infected CEM cells.
[b]The cellular toxicity was measured in CEM cells.
[c]The 50% inhibitory dose.
[d]The 50% tissue culture inhibitory dose.

What is claimed is:

1. A process for producing a 2',3'-dideoxy-2',3'-didehydronucleoside represented by the formula

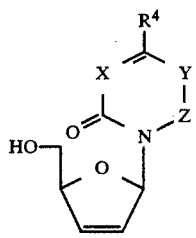

wherein the base moiety is a member selected from the group of unsubstituted and substituted bases consisting of pyrimidine, aza-pyrimidine, and deaza-pyrimidine; X is selected from N and C-H; Y is selected from C-R$^5$ and N; Z is selected from C-H and N; R$^4$ is selected from OH and NH$_2$; and R$^5$ is selected from H, unsubstituted and halo-substituted alkyl having the formula C$_n$H$_{2n}$A, and unsubstituted and halo-substituted alkenyl having the formula —(CH$_2$)$_m$-CH=CHA, wherein m is an integer selected from 0, 1, 2 and 3, n is an integer selected from 1, 2, and 3 and A is selected from H, F, Cl, Br, and I, comprising the steps of:

(a) reacting, with a strong base, a 2'-deoxynucleoside represented by the formula

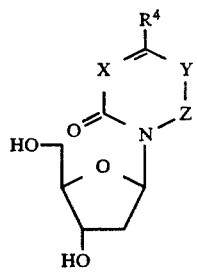

to form a reactive 2,3'-anhydro-2'-deoxynucleoside intermediate represented by the formula

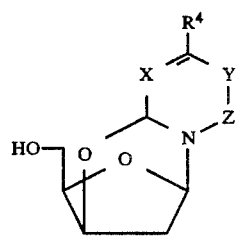

and (b) converting in the presence of base selected from non-nucleophilic and nucleophilic bases said reactive 2,3'-anhydro-2'-deoxynucleoside from step (a) above to said 2',3'-dideoxy-2',3'-didehydronucleoside.

2. A process according to claim 1 wherein said non-nucleophilic base in step (b) is tetrabutylammonium fluoride (TBAF).

3. A process according to claim 1 wherein said nucleophilic base in step (b) is selected from KOtBu, NaOH and KOH.

4. A process according to claim 3 wherein the base is an unsubstituted and substituted pyrimidine base.

5. A process according to claim 1 wherein the pyrimidine base is selected from thymine (5-methyl-2,4-dihydroxypyrimidine), cytosine (2-hydroxy-4-aminopyrimidine), uracil (2,4-dihydroxypyrimidine), and 5-ethyl- and 5-vinyl- and 5-halovinyl- and 5-halomethyl- and 5-haloethyl-2,4-dihydroxypyrimidin-3-yl.

6. A process according to claim 5 wherein the base is thymine.

* * * * *